US012004904B2

(12) United States Patent
Van Neer et al.

(10) Patent No.: US 12,004,904 B2
(45) Date of Patent: Jun. 11, 2024

(54) CONFIGURABLE ADHESIVE DEVICE AND METHOD

(71) Applicant: Nederlandse Organisatie voor toegepast-natuurwetenschappelijk onderzoek TNO, 's-Gravenhage (NL)

(72) Inventors: Paul Louis Maria Joseph Van Neer, Bergschenhoek (NL); Arno Willem Frederik Volker, Delft (NL); Hylke Broer Akkerman, Rosmalen (NL); Gerwin Hermanus Gelinck, Valkenswaard (NL); Antonius Maria Bernardus Van Mol, Veldhoven (NL); Arthur Perry Berkhoff, Doetinchem (NL)

(73) Assignee: Nederlandse Organisatie voor toegepast-natuurwetenschappelijk onderzoek TNO, 's-Gravenhage (NL)

( * ) Notice: Subject to any disclaimer, the term of this patent is extended or adjusted under 35 U.S.C. 154(b) by 399 days.

(21) Appl. No.: 17/599,653

(22) PCT Filed: Apr. 6, 2020

(86) PCT No.: PCT/NL2020/050232
§ 371 (c)(1),
(2) Date: Sep. 29, 2021

(87) PCT Pub. No.: WO2020/209713
PCT Pub. Date: Oct. 15, 2020

(65) Prior Publication Data
US 2022/0192633 A1 Jun. 23, 2022

(30) Foreign Application Priority Data
Apr. 8, 2019 (EP) .................... 19167821

(51) Int. Cl.
*A61B 8/00* (2006.01)
*F16B 47/00* (2006.01)
(Continued)

(52) U.S. Cl.
CPC ............ *A61B 8/4209* (2013.01); *F16B 47/00* (2013.01); *H10N 30/2047* (2023.02)

(58) Field of Classification Search
CPC ....... A61B 5/252; A61B 8/4209; F16B 47/00; H10N 30/2047
See application file for complete search history.

(56) References Cited

U.S. PATENT DOCUMENTS

| 3,514,065 A | 5/1970 | Litt et al. |
| 2006/0232167 A1 | 10/2006 | Jordan |
| 2011/0280755 A1 | 11/2011 | Wackerle et al. |

FOREIGN PATENT DOCUMENTS

| CN | 200974418 Y | 11/2007 |
| CN | 203171637 U | 9/2013 |

(Continued)

OTHER PUBLICATIONS

European Patent Office, International Search Report in corresponding International Application No. PCT/NL2020/050232, dated Jun. 23, 2020 (2 pages).

(Continued)

*Primary Examiner* — Michael T Rozanski
(74) *Attorney, Agent, or Firm* — Leydig, Voit & Mayer, Ltd.

(57) ABSTRACT

A device (100) and method for adhering by suction to a target surface (200). The device has a substrate (20) with a contact surface (20*a*) for contacting the device (100) to the target surface (200). A plurality of pocket (10) are formed by respective pocket surfaces (10*a*) concavely extending into the contact surface (20*a*). The pockets (10) have an open side (10*b*) facing and being closed off by the target surface (200). A flexible membrane (15) forms at least part of the pocket surface (10*a*). An actuator (40) is configured to actuate the flexible membrane (15). A one-way valve (30) through the pocket surface (10*a*) is configured to direct a contents of the pocket (10) via the one-way valve (30) to an environment (300).

19 Claims, 5 Drawing Sheets

(51) Int. Cl.
*H01L 41/09* (2006.01)
*H10N 30/20* (2023.01)

(56) References Cited

FOREIGN PATENT DOCUMENTS

| | | |
|---|---|---|
| CN | 104179782 A | 12/2014 |
| EP | 2438302 | 4/2012 |
| JP | 2004-353493 | 12/2004 |
| JP | 2012528981 A | 11/2012 |
| JP | 5502079 B2 | 5/2014 |
| TW | 201742188 A | 12/2017 |

OTHER PUBLICATIONS

China National Intellectual Property Administration, Office Action in corresponding Chinese Application No. 202080032304.X dated Feb. 13, 2023.
Bingshan Hu et al., "Optimal Design and Simulation of a Microsuction Cup Integrated with a Valveless Piezoelectric Pump for Robotics," Hindawi, Shock and Vibration, vol. 2018, Article ID 7987502, 16 pages https://doi.org/10.1155/2018/7987502.

CONFIGURABLE ADHESIVE DEVICE AND METHOD

CROSS-REFERENCE TO RELATED APPLICATIONS

This patent application is a U.S. National Phase of PCT International Application No. PCT/NL2020/050232, filed Apr. 6, 2020, which claims priority to European Application No. 19167821.8, filed Apr. 8, 2019, which are both expressly incorporated by reference in their entireties, including any references contained therein.

TECHNICAL FIELD AND BACKGROUND

This invention relates to devices for adhering to a target surface and related methods of use.

Various methods exist for fastening devices. For example, a device may be fastened to a surface using nails or screws. However this may damage the surface and is obviously not suitable for applying a device to the skin. Alternatively, substances such as glue may be used. However, this may be too permanent. Non-destructive and/or temporary connection may be provided, e.g. using suction cups. However, these are typically not suitable for all surfaces, e.g. can get easily disconnected. Alternatively still, sticky substances and/or tape can be used to adhere a device.

For example, U.S. Pat. No. 5,394,877A describes an ultrasound medical diagnostic device having a coupling medium providing self-adherence to a patient. As described in the prior art, a contact medium structure attachable to externally-applied medical diagnostic devices provides self-adherence of the medical device to the skin of a patient eliminating the need for belts or similar means. Specifically, a mesh-reinforced hydrogel film is used which adheres to the device and extends beyond the perimeter of the device to provide additional adhesiveness and compliance with the contour of the patient's body. A support element associated with and extending beyond the perimeter of the medical device adheres to the contact medium and provides adjustability of the extended hydrogel film relative to the patient's skin. Unfortunately, adhesive properties of the known hydrogel film may be difficult to control and the gel may leave undesired residue.

There remains a need for further improvements in controlling adhesion of devices for forming (temporary) connections with a variety of surfaces.

SUMMARY

Aspects of the present disclosure relate to devices and methods for adhering to a target surface. As described herein, the adhesion force may be provided by suction. For example, a pocket is formed by an area recessed into a contact surface. The pocket may be closed off by the target surface when the device is brought in contact therewith. In this way, the pocket may act as a sort of suction cup. It will be appreciated that the use of suction as the mode of adhesion may avoid the occurrence of damage and/or formation of residue. As described herein, a contents of the pocket, e.g. air, may be actively removed from the pocket to create or maintain a relatively low pressure in the pocket. By actively controlling the suction mechanism, the adhesion may be controlled making the device suitable for a variety of target surfaces. Preferably, a vibrating flexible membrane is used to push the air out of the pocket. For example, the membrane can be part of a wall bounding the pocket. In this way a relatively simple pumping mechanism can be formed, e.g. applicable in a thin (sheet) device. Advantageously, a one way valve can be used to allow the air out of the pocket while preventing the air from flowing back into the pocket. In this way, a relatively low pressure in the pocket can be more easily built up and maintained. By providing a flexible contact surface and/or a flexible substrate the device may adapt its shape to a variety of target surfaces whether flat, curved or otherwise shaped. By providing multiple pockets with respective flexible membranes and one-way valves, a self-adhesive large area device may be formed, for example a self-adhering ultrasonic (sheet) device. Preferably, the one or more valves are formed in the vibrating membrane. For example, a flap in the vibrating membrane can be used as a one-way valve to form a relatively compact and easily constructed device.

BRIEF DESCRIPTION OF DRAWINGS

These and other features, aspects, and advantages of the apparatus, systems and methods of the present disclosure will become better understood from the following description, appended claims, and accompanying drawing wherein:

DESCRIPTION OF EMBODIMENTS

Figure 1A:
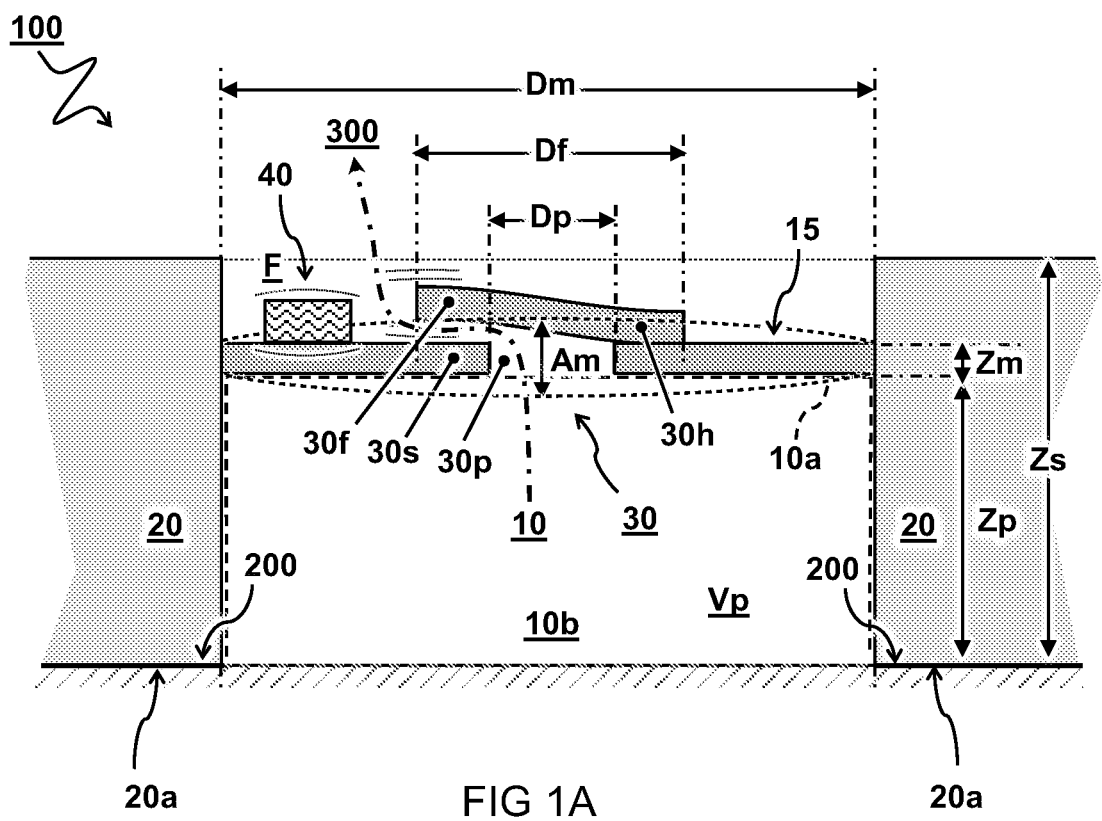
FIG. 1A schematically shows a cross-sectional view of a device for adhering by suction to a target surface.

Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise it will be understood that when a connection between structures or components is described, this connection may be established directly or through intermediate structures or components unless specified otherwise.

The invention is described more fully hereinafter with reference to the accompanying drawings, in which embodiments of the invention are shown. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

FIG. 1A schematically shows a cross-sectional view of a device 100 for adhering by suction to a target surface 200.

In some embodiments, the device 100 comprises a substrate 20 having a contact surface 20a for contacting the device 100 to the target surface 200. In the embodiment shown, a pocket 10 is formed by a pocket surface 10a extending, e.g. concavely, into the contact surface 20a. In other words the pocket 10 may be formed by an area recessed into the contact surface 20a. The pocket has an open side 10b which in use may face the target surface 200. In this way, the target surface may close off the pocket 10.

In some embodiments, the device comprises a flexible membrane 15 forming at least part of the pocket surface 10a. In other or further embodiments, e.g. as shown, an actuator 40 is integrated as part of the device. In one embodiment, the actuator 40 is configured to actuate the flexible membrane 15. In a preferred embodiment, a one-way valve 30 extends through the pocket surface 10a. In particular, the one-way valve 30 is preferably configured to direct the contents of the pocket 10 via the one-way valve 30 to an environment 300. In principle, the environment 300 may be formed by any (sufficiently large) volume on the other side of the one-way valve 30, e.g. typically the external surroundings of the device. In a preferred embodiment, the at least one actuator 40 actuating the flexible membranes 15 of the pockets causes the contents of the pockets to be pumped out via the one-way valves 30. Accordingly, the suction between the contact surface 20a of the device and the target surface 200 can be established and/or maintained.

In some embodiments, the target surface 200 may be a (relatively) flat surface. Accordingly, the contact surface 20a can be similarly flat for abutting the target surface 200. In other or further embodiments, e.g. shown in FIG. 1B, the target surface 200 may be curved. Accordingly, the contact surface 20a may be similarly curved and/or the contact surface 20a may be flexible and/or resilient to conform its shape to that of a wide variety of target surfaces which may be curved, or having any other shape. Flexibility is typically understood as the ability of a material to deform elastically under the influence of applied stress, and return to its original shape when the stress is removed.

In some embodiments, the substrate 20 is formed as a sheet. For example, the substrate 20 is a flexible sheet which can deform to adapt to the contact surface 20a. In other or further embodiments, the substrate 20 is relatively thin and/or comprises a relatively flexible material to allow deformation. For example, the substrate 20 has a relatively low thickness "Zs" of less than one centimeter, less than half a centimeter, less than three millimeters, or even less, e.g. between 0.1-2 mm. Typically, the substrate 20 or sheet has relatively high surface area, i.e. having a dimension along its surface much higher than its thickness "Zs", e.g. by a factor ten, hundred, thousand, or more. Of course, the substrate 20 may also have other form factors.

Typically, the flexible membrane 15 is fixed to the substrate 20. In some embodiments, the flexible membrane 15 is attached to the substrate 20 by lamination. In other or further embodiments, the flexible membrane 15 may be formed as an integral part of the substrate 20. For example, the flexible membrane 15 is formed by removing part of the substrate 20 to excavate the pocket 10. Alternatively, or additionally, the one or more pockets 10 with flexible membranes 15 are formed together with the substrate 20, e.g. by molding. Also other ways can be envisaged for fixating the flexible membrane 15 to the substrate 20, e.g. using an adhesive, melting, et cetera. In some embodiments, the substrate 20 and the flexible membrane 15 are formed of the same material. Alternatively, the substrate 20 may be of a different material.

When the pocket 10 is closed off by the target surface 200, it is preferred that an exclusive passage 30p remains extending through the pocket surface 10a, which passage is configured to direct the contents of the pocket 10 via the one-way valve 30 to the environment 300. In the embodiments shown, a thick dash-dotted arrow is used to indicate the exclusive (or preferential) flow direction from the pocket 10 to the external surrounding 300 through the one-way valve 30 via the passage 30p. In the embodiment shown, the one-way valve 30 extends through the flexible membrane 15, but the valve may also extend through other parts of the pocket surface 10a as will be described later e.g. with reference to FIGS. 3A-3B.

In some embodiments, the pocket 10 may act like a reservoir for a contents of the pocket, e.g. air or another fluid. As described herein, the pocket 10 comprises a pocket surface 10a bounding the pocket 10. In some embodiments, e.g. as shown, the pocket surface 10a comprises or is formed by the substrate 20 and the flexible membrane 15. In a preferred embodiment, the flexible membrane 15 is opposite to the open side of the pocket 10b. Also other relative positioning may be envisaged. In some embodiments, e.g. as shown, the flexible membrane 15 separates the pocket 10 from the environment 300, e.g. when the one-way valve 30 extends through the flexible membrane 15.

Typically, a one-way valve may be configured to allow contents to flow more easily in one direction than the other, in this case more easily outwards from the pocket 10 to the environment 300 than inwards from the environment 300 to the pocket 10. For example, a (fluid) flow resistance in a direction into the pocket 10 is much higher than in a direction out of the pocket 10, e.g. higher by at least a factor ten, preferably at least a factor fifty, or more than a factor hundred. The more the one-way valve 30 resists fluid flowing back into the pocket 10, the better the under pressure in the pocket 10 may be effected and/or maintained. In some embodiments, the one-way valve 30 allows the contents of the pocket 10 to flow through it exclusively in one direction, i.e. out to the environment 300, while substantially preventing the contents to flow back in the other direction, i.e. into the pocket.

Figure 3A:
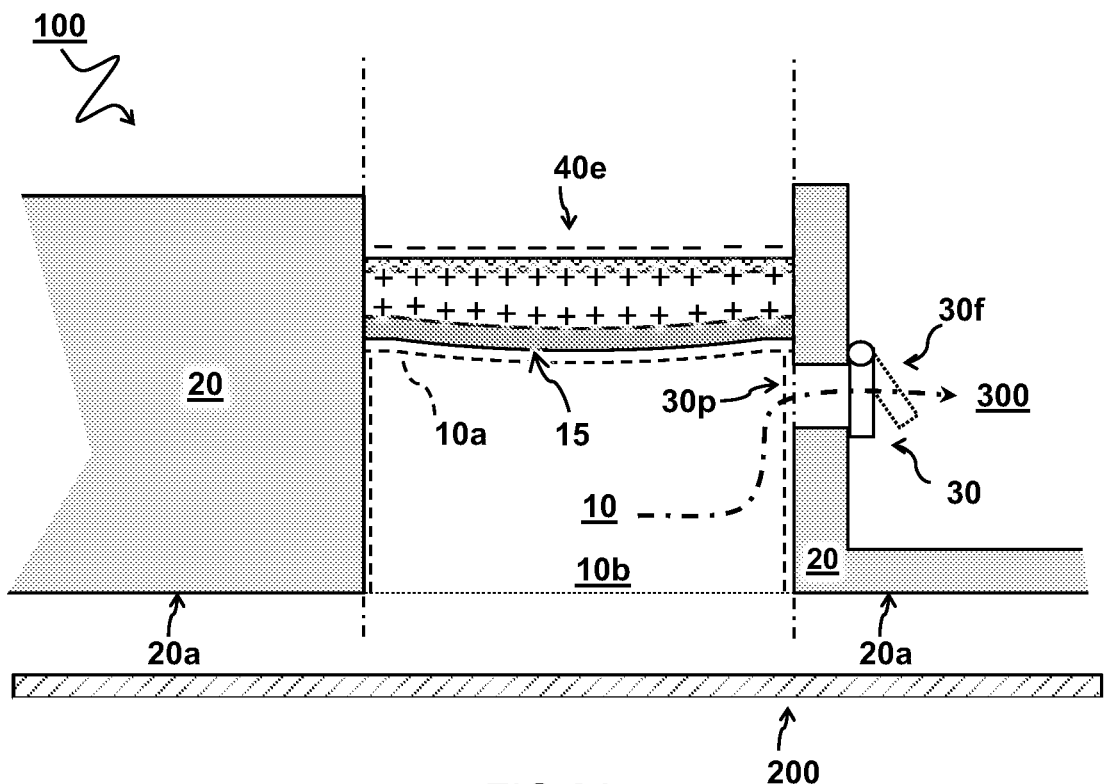
FIG. 3A illustrates an electro-static actuator configured to actuate the flexible membrane.

In a preferred embodiment, e.g. as shown, the one-way valve 30 is formed through the flexible membrane 15. In another or further preferred embodiment, the one-way valve 30 comprises, or is formed by, a flap 30f configured to open a passage 30p out of the pocket 10 when air flows in a direction out of the pocket 10 and closes in an opposite direction. For example, the flap 30f may cover a passage 30p through the flexible membrane 15, e.g. as shown in FIG. 1A; or through another passage out of the pocket, e.g. as shown in FIG. 3A. Typically, a dimension of the flap "Df" along the surface of the flexible membrane 15 is larger than a cross-surface dimension of the passage "Dp", which the flap covers, e.g. larger by at least a factor 1.1 or 1.2, e.g. up to a factor two or more. In some embodiments, the flap comprises or forms part of a hinge 30h attaching one end of the flap 30f to the flexible membrane or to the substrate 20. Another end of the flap may abut an opposing part 30s of the flexible membrane (or substrate), which may act a valve seat against which the flap 30f may rest to close the passage 30p. In a preferred embodiment, the flexible membrane 15 and the flap 30f of the one-way valve 30 are made of the same material e.g. to avoid triboelectric effects.

In some embodiments, the device 100 may, in use, contact a target surface 200. Accordingly the target surface 200 may at least partially close an open side of a pocket 10b of the device. The flexible membrane 15, forming at least part of the pocket surface, may be actuated by the actuator, or otherwise. In this way the membrane may contribute to directing a contents of the pocket 10 to an external environment 300, e.g. via a one-way valve 30. In other or further embodiments, the device 100 may be detached or turned off by air leaking back into the pocket 10 from the environment 300. For example, some leakage may occur back through the one-way valve 30, or through the (permeable) flexible membrane 15, or otherwise, e.g. a small opening in the device. In other or further embodiments, the device may be detached by actively switching the device to open the pocket, e.g. switching operation of the one-way valve 30, or using a separate release valve (not shown).

Figure 1B:
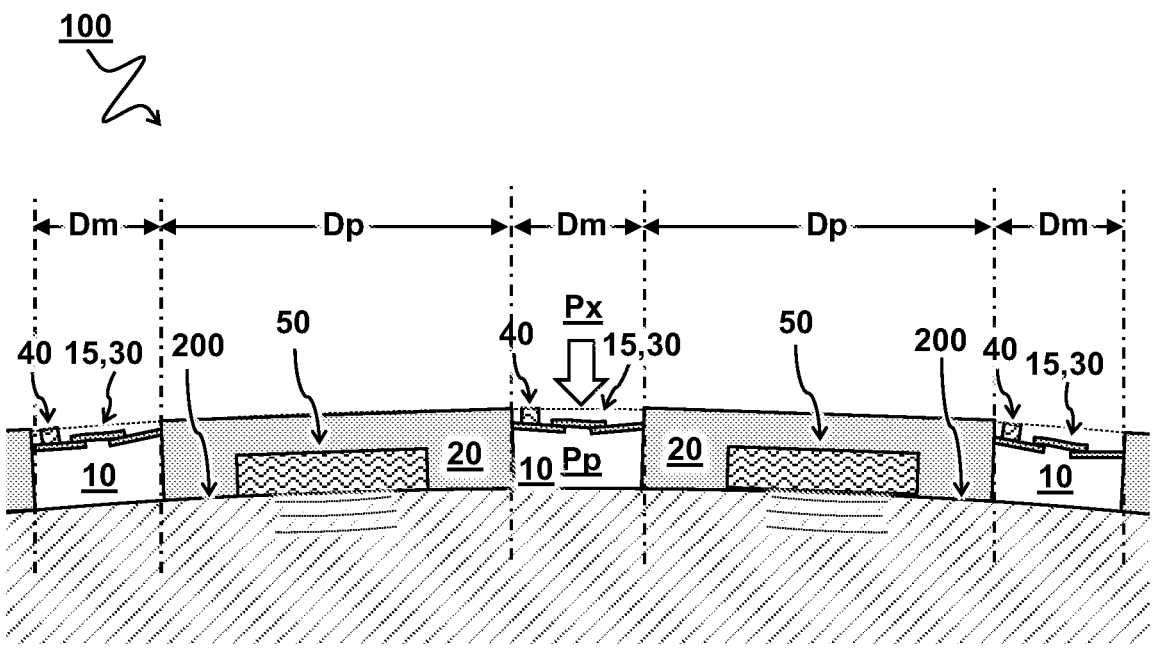
FIG. 1B illustrates the device comprising multiple pockets with respective flexible membranes and one-way valves.

In a preferred embodiment, e.g. as illustrated in FIG. 1B, suction of the device 100 is effected by developing or maintaining a relatively low pressure "Pp" in the pocket 10, e.g. compared to an environmental pressure "Px". Without being bound by theory, a pressure differential between the environment 300 and the pocket 10 may cause a net force on the device towards the target surface 200. In the embodiments shown, the flexible membrane 15 is actuated to oscillate while forming part of the pocket surface 10a. In this way, the flexible membrane 15 may act like a pump pushing contents of the pocket 10, e.g. air, out from the pocket 10 through the one-way valve 30. For example, the one-way valve 30 may help to develop or maintain the relatively low pressure inside the pocket 10 (compared to the environment 300), causing the flexible membrane 15 to adhere (stick) to the target surface 200 by suction.

Preferably, a volume of the pocket "Vp" should be sufficiently large to allow the pocket 10 to effectively function as a reservoir for air, e.g. taking into account possible leakage of air back into the pocket. For example, a volume of the pocket "Vp" is on the order of cubed millimeter ($mm^3$) or less, for example between 0.01-100 $mm^3$, preferably between 0.05-20 $mm^3$, e.g. between one and ten millimeters cubed. To achieve sufficient volume, in some embodiments, a depth of the pocket "Zp" is between a ten micrometers and five millimeters, preferably between twenty and two-hundred micrometers, more preferably between fifty and a hundred micrometers. For example, a depth of the pocket "Zp" may be determined or limited by a thickness "Zs" of the substrate 20. By keeping the pocket depth relatively low, the substrate can be kept relatively thin which may help to keep the device conformable/flexible. Of course, a volume of the pocket "Vp" may also be related to its diameter which may be the same as a diameter of the flexible membrane 15. For example, a diameter of the flexible membrane "Dm" may be between hundred micrometers and five millimeters, preferably between three-hundred micrometers and one millimeter, e.g. eight-hundred micrometers. In some embodiments, a surface area of the flexible membrane 15 is on the order of a square millimeter ($mm^2$) up to one square centimeter ($cm^2$), for example between 0.1 $mm^2$ 1 $cm^2$, preferably between 0.5-10 $mm^2$, e.g. between one and five millimeters squared. The larger the surface area of the flexible membrane 15, the more air it pushes out of the pocket to the external surrounding 300 through the one-way valve 30.

In one embodiment, e.g. as shown, the flexible membrane 15 is configured to oscillate inside or adjacent the pocket 10 with an amplitude "Am". In some embodiments, the (maximum) amplitude "Am" of the oscillation of the flexible membrane 15 is on the order of a few micrometers, e.g. between 10-1000 µm, preferably between fifty and hundred micrometers. In some embodiments, the amplitude "Am" of the flexible membrane 15 in combination with the surface area of the flexible membrane 15 determines the amount of air that the flexible membrane 15 pushes out of the pocket 10, i.e. the volume of the pocket "Vp".

Preferably, the flexible membrane 15 has relatively high flexibility, stretchability and/or elasticity to perform its function, i.e. expand into the pocket 10 during the oscillations with relatively large amplitude "Am" to remove its contents. Preferably, the flexible membrane 15 is more flexible than the substrate 20, i.e. having a relatively low flexural rigidity compared to the flexible membrane 15, e.g. lower by at least a factor two, five, ten, or more. Typically, the flexural rigidity of the flexible membrane 15 depends mainly on its elastic modulus and thickness. In some embodiments, the flexible membrane 15 has an elastic modulus e.g. Young's modulus less than five Gigapascals, e.g. between 0.01 (rubber) 5 GPa. Suitable materials may e.g. include Polyethylene Terephthalate PET with typical Young's modulus between 2-2.7 GPa. Other or further possible flexible membrane 15 materials may include e.g. Polyethylene Naphthalate PEN. The teachings may particularly provide benefit also to highly stretchable materials such as Thermoplastic Urethane TPU. For example, the Young's modulus of the flexible membrane 15 may be less than one Gigapascal e.g. measured at room temperature of 25° C.

In some embodiments, the flexible membrane 15 has relatively high stretchability and/or elasticity along one or more (in-plane) directions to allow expanding its size e.g. length along the said one or more directions without breaking; by at least a factor 1.1 or 1.2, e.g. up to a factor two or more. In other or further embodiments, a thickness of the flexible membrane "Zm" is between one and thousand micrometers, preferably between ten and two-hundred micrometers, more preferably between fifty and hundred micrometers. By providing a relatively small thickness of the flexible membrane "Zm", e.g. ten micrometers, the flexible membrane 15 can easily be vibrated by the actuator 40 due to its low flexural rigidity. Alternatively, higher thickness of the flexible membrane "Zm" may provide lower air permeability of the flexible membrane 15. Accordingly, higher under-pressure can be formed in the pocket 10 to open the one-way valve 30.

In some embodiments, the amplitude "Am" of the flexible membrane 15 is determined by the frequency "F" of the actuator 40. In one embodiment, the frequency "F" of the actuator 40 is on the order of one kilohertz up to one megahertz, for example a hundred kilohertz, configured to actuate the flexible membrane 15. In a preferred embodiment, the actuator 40 actuates the flexible membrane 15 with frequency "F" at or near the resonance frequency of the flexible membrane 15. In some embodiments, e.g. as shown in FIG. 1A, the actuator 40 is disposed on the flexible membrane 15.

In some embodiments, e.g. as shown in FIG. 1B, the device 100 comprises multiple pockets 10 with respective flexible membranes 15 and one-way valves 30. In some embodiments, each flexible membrane 15 is actuated by a respective actuator 40. In other or further embodiments, one or more actuators may be configured to actuate multiple flexible membranes 15 (not shown).

In some embodiments, active components 50 such as acoustic transducers, may be disposed between the pockets 10. The active components 50 may be the same or distinct from the one or more actuators 40 actuating the one or more flexible membranes 15. For example, the active components 50 may also be (separate) acoustic components, e.g. for inspecting the target surface 200, or a body below the target surface 200. Also other types of active components 50 may be envisaged, e.g. light emitting devices, touch sensitive devices, et cetera.

In a preferred embodiment, the pockets 10 are disposed away from each other with a distance between the pockets "Dp" on the order of a few millimeters up to a few centimeters, or more, depending on the diameter of the flexible membrane "Dm" and the volume of the pocket "Vp". For example, if the volume of the pocket "Vp" is on the order of a few cubic micrometers e.g. up to one cubic millimeter, then a matrix of many pockets 10 may be provided, e.g. more than ten, twenty, fifty, or even more than a hundred (micro) pockets 10 to hold the device 100 to the target surface 200. Alternatively, if the volume of each pocket "Vp" is on the order of a few cubic millimeters, or even a cubic centimeter, then a fewer number of pockets 10 may be needed to hold the device 100.

Figure 4A:
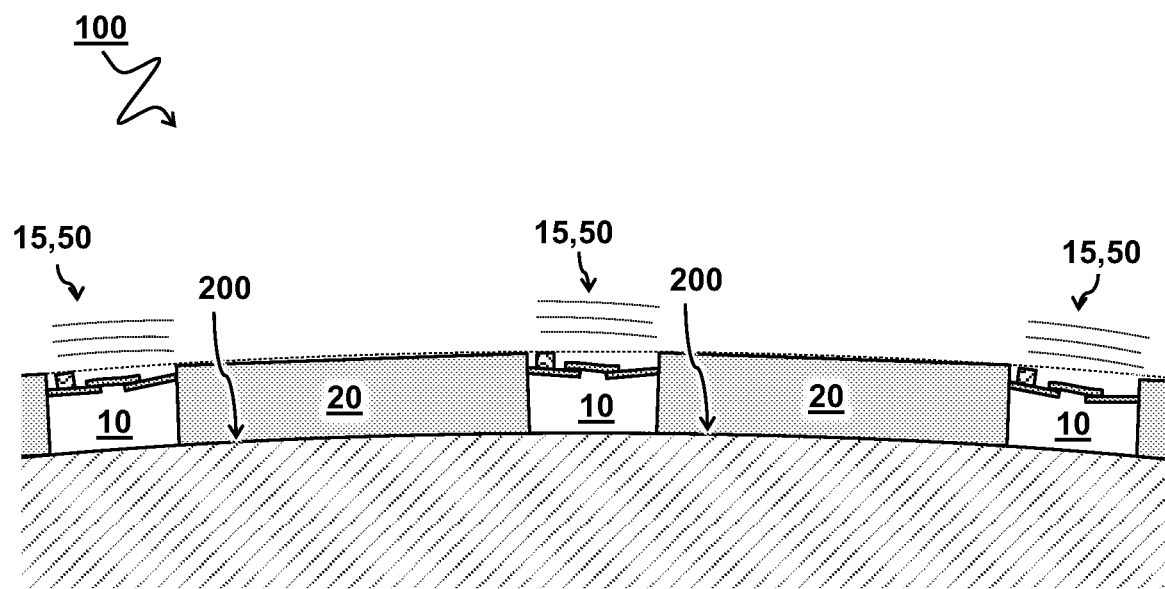
FIG. 4A illustrates a device wherein the flexible membranes also function as active components.
Figure 4B:
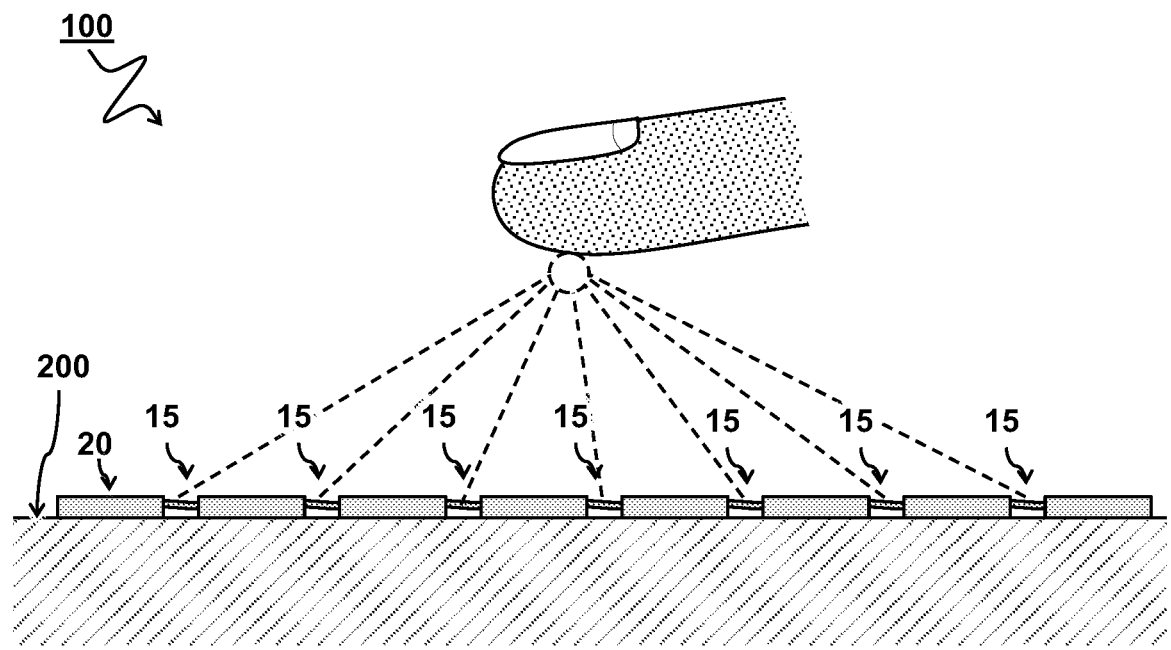
FIG. 4B illustrates a possible application for a self-adhering ultrasonic device.

In a preferred embodiment, the device is an acoustic device 100 for acoustic interaction with a target, e.g. inspecting a body or interaction with an object such as a finger held above the device (FIG. 4B). In one embodiment, the device comprises an acoustic transducer 50 (which may be separate from the actuator 40, or the same) configured to transceive acoustic signals for the acoustic interaction with the target, e.g. inspection of the body via the contact surface 20a or interaction with another object. In some embodiments, the one-way valve 30 is configured to direct the contents of the pocket 10 via the one-way valve 30 for adhering the device to the target surface 200 during the acoustic interaction with the target. In one embodiment, the acoustic device comprises a controller for controlling the actuators and/or acoustic transducers. In some embodiments, the controller is configured to transceive electrical signals to and/or from the acoustic transducers. In one embodiment, the electrical signals are configured to cause the transducers to emit acoustic waves, e.g. into the body via the target surface 200, or in the air above the device. In another or further embodiment, electric signals are received from the transducers. For example, acoustic waves received by the transducers can be used to form an (ultrasound) image of the body. As described herein, the body can be of a subject, e.g. to inspect a human physiology; or the body of an object, e.g. to inspect for structural integrity.

Figure 2A:
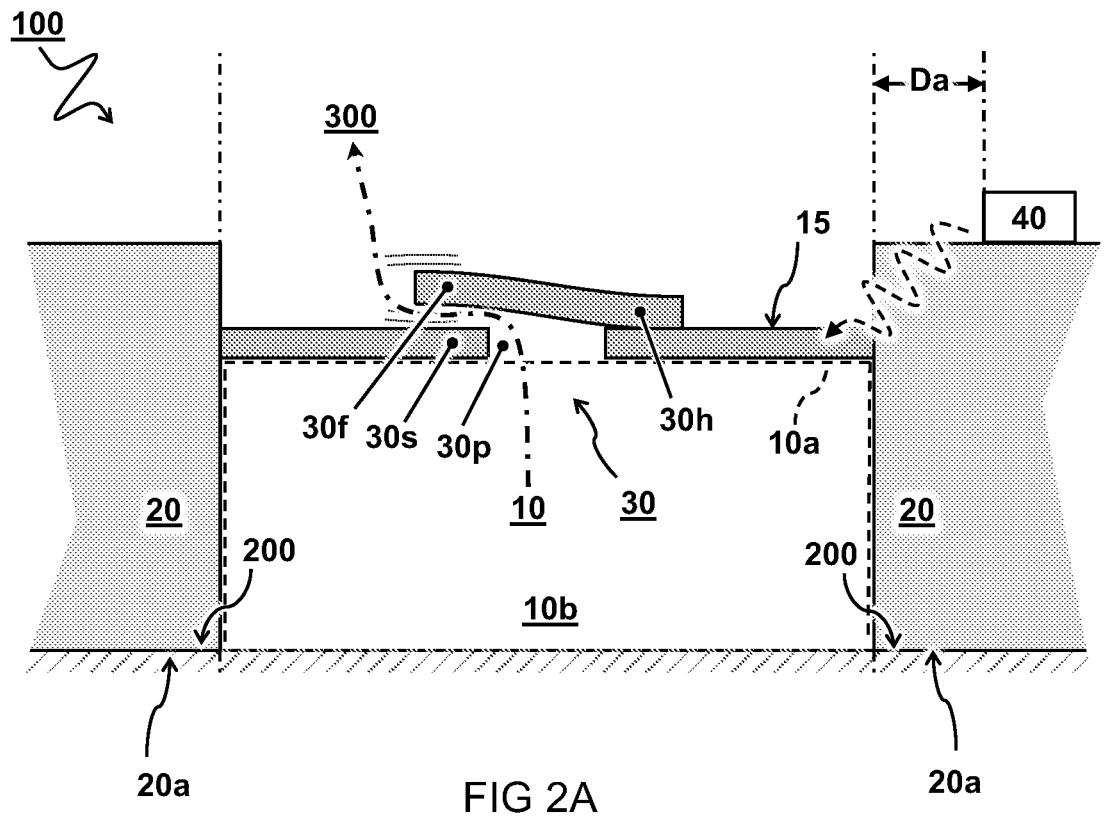
FIG. 2A illustrates a device with alternative positioning of an actuator.

FIG. 2A illustrates an embodiment wherein the actuator 40 is disposed on the substrate 20 configured to actuate the flexible membrane 15. Preferably, a distance "Da" between the membrane 15 and respective actuator 40 is relatively small, e.g. less than one centimeter, less than half a centimeter, or even less than one millimeter (along the substrate surface). Accordingly, the flexible membrane 15 is in vibrational communication with the actuator 40 (directly or via intermediate structures such as the substrate 20).

Figure 2B:
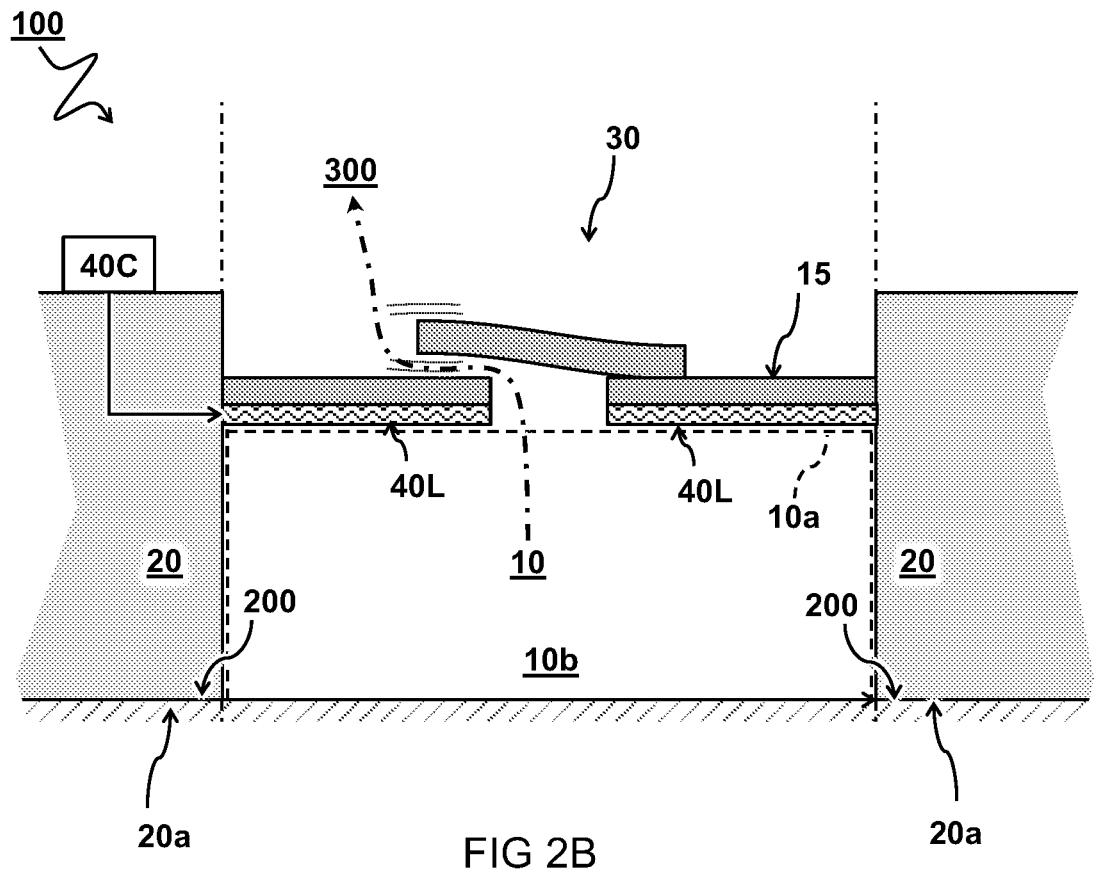
FIG. 2B illustrates an actuator comprising a piezoelectric layer adhered to a flexible membrane.

FIG. 2B illustrates an embodiment wherein the actuator 40 comprises, or is formed by, a piezoelectric layer 40L adhered to the flexible membrane 15. For example, the actuation may be effected by expansion and/or contraction of the piezoelectric layer 40L with respect to the flexible membrane 15, e.g. preferably along the surface of the flexible membrane 15. For example, the stack of the flexible membrane 15 and piezoelectric layer 40L may deform as a result of said relative expansion and/or contraction. In another or further embodiment, the device further comprises a controller 4C configured to energize the piezoelectric layer 40L for actuating the flexible membrane 15. Typically, the piezoelectric layer 40L is also stretchable and flexible to retain the dynamic characteristics of the flexible membrane 15. For example, the piezoelectric material may be polymer based. In some embodiments, the piezoelectric layer 40L may be molded into the substrate 30, laminated onto the substrate 20, or otherwise fixed to the substrate 30 configured to vibrate the flexible membrane 15 by the piezoelectric layer 40L while their ends are fixed to the substrate 20.

Figure 3B:
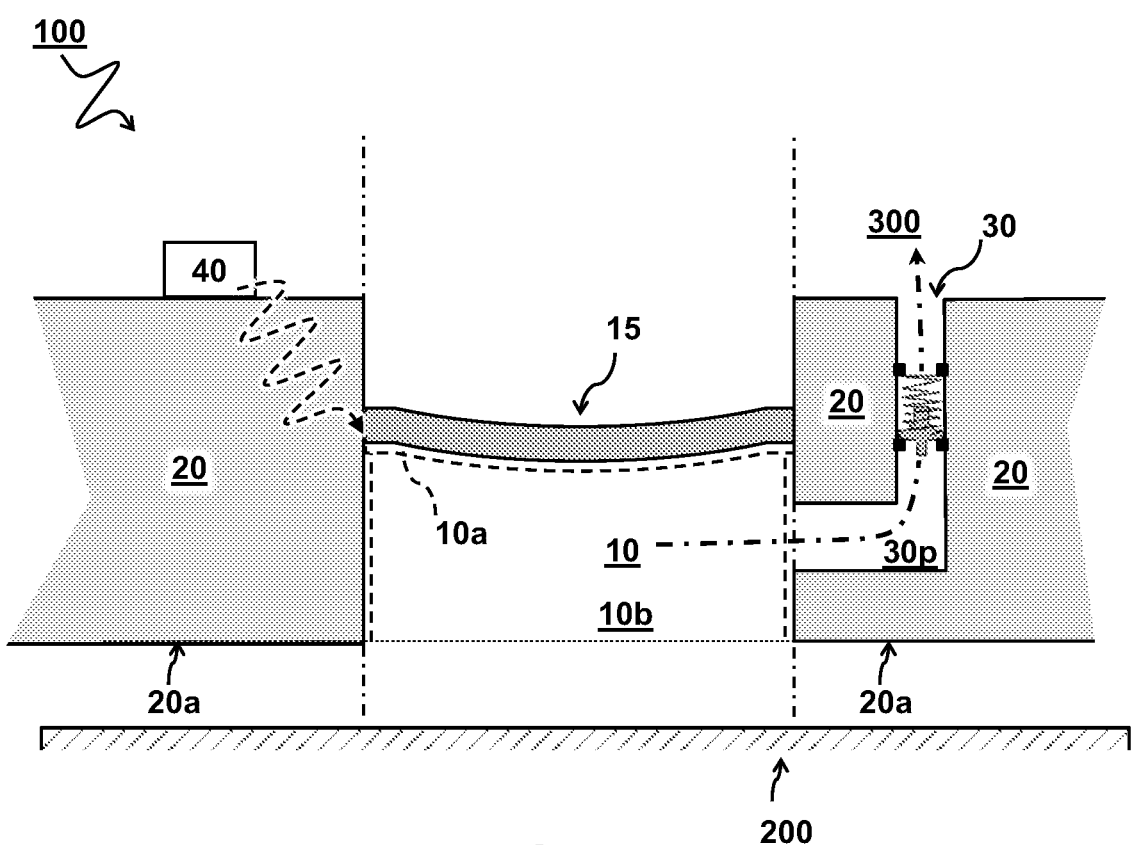
FIG. 3B illustrates a one-way valve formed by a valve disposed in a relatively long passage extending through the substrate.

FIG. 3A illustrates an embodiment wherein an electrostatic actuator 40e is configured to actuate the flexible membrane 15. In some embodiments, e.g. as shown, a passage 30p (here through the substrate 20) may be closed off by a flap 30f to form the one-way valve 30, or alternative types of one-way valves 30 may be used. Of course also other types of (one-way) valves may be used. For example, FIG. 3B illustrates an embodiment wherein the one-way valve 30 is formed by a check-valve. For example, e.g. as shown, the passage 30p is extended through the substrate 20 and the one-way valve 30 is formed by a check-valve system comprising a spring and a valve disk disposed in the passage 30p. Also other types of one-way valves, or valves having a preferred direction of flow can be envisaged. In one embodiment (not shown), the one way valve is formed by or comprises an asymmetric orifice which causes the flow speed or flow resistance in one direction to be lower than in the other direction (e.g. at equal pressure difference over the membrane). For example, the one way valve may be formed by an asymmetric orifice in an elongate channel or tube.

FIG. 4A illustrates another embodiment wherein the device 100 comprises multiple pockets 10. In one embodiment, e.g. as shown, the flexible membranes 15 also function as active components 50 for another function besides adhesion. For example, a respective one or more flexible membranes 15 vibrating over respective pockets 10 and used for adhering the device 100 may themselves form active components 50, e.g. acoustic transducers emitting sound waves upward (or downward) and away from the target surface 200. This may be contrasted, e.g. with the embodiment of FIG. 1B, where the active components 50 are separate and in between the pockets 10. Also combinations are possible.

FIG. 4B illustrates a possible application for a self-adhering ultrasonic device 100. In some embodiments, sound waves originating from different sources may be used, e.g. constructively interfere. In one embodiment, e.g. as shown, the different sources may be formed by the respective flexible membranes 15. In another or further embodiment (not shown), also other or further sources such as the active components 50 can be used for constructive or destructive interference of sound waves at some particular location. In one embodiment, e.g. as shown, the sound waves may constructively interfere to form a haptic interface, e.g. virtual button in mid air. Possible applications may include a virtual reality interface.

Figure 5A:
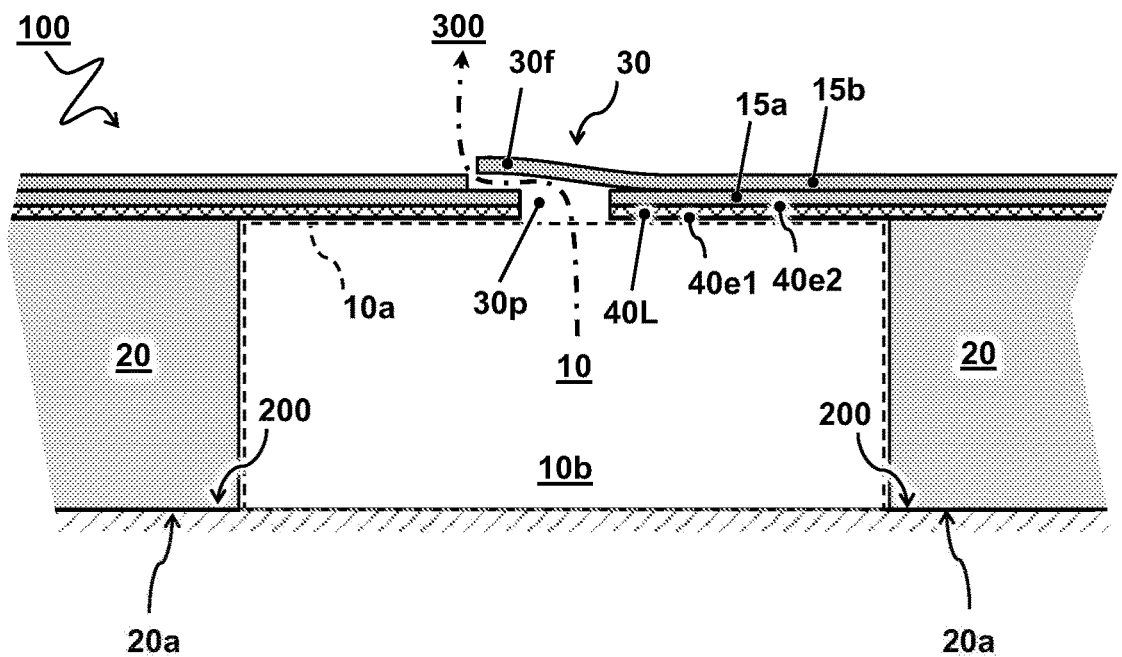
FIG. 5A illustrates a cross-sectional view of a device wherein the flexible membrane is attached by lamination onto the substrate.
Figure 5B:
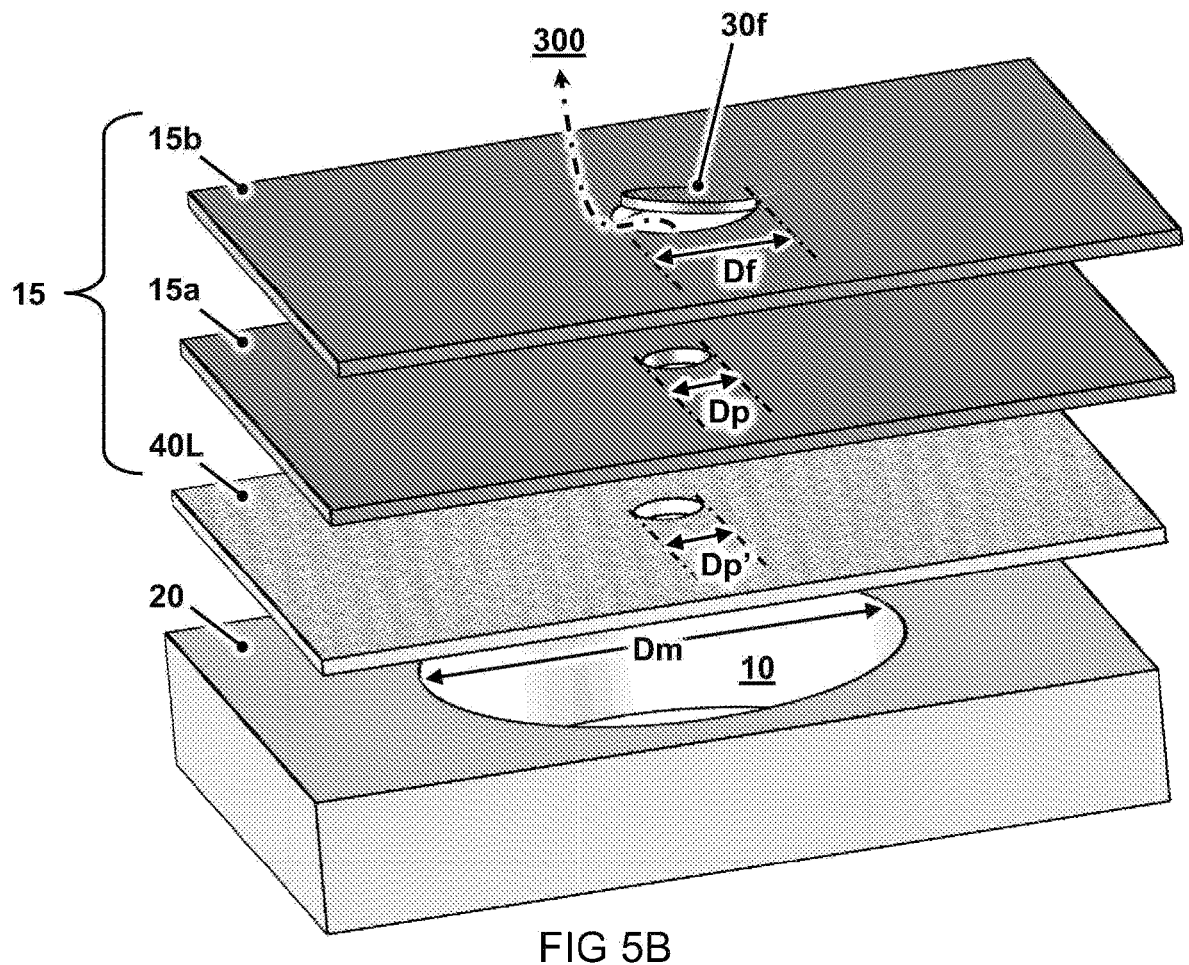
FIG. 5B illustrates a corresponding exploded perspective view of the embodiment shown in FIG. 5A.

FIG. 5A illustrates a cross-section view of an embodiment wherein the flexible membrane 15 is attached by lamination onto the substrate 20. FIG. 5B illustrates a corresponding exploded perspective view of the embodiment.

In one embodiment, e.g. as shown, the flexible membrane 15 comprises a first membrane layer 15a; and a second membrane layer 15b adhered to the first membrane layer 15a. In another or further embodiment, the one-way valve 30 is formed by a flap 30f cut out from the first membrane layer 15a covering a passage 30p cut out from the second membrane layer 15b. Typically the flap 30p may be larger than the passage, e.g. the flap diameter "Df" is larger than the passage diameter "Dp" by at least a factor 1.1, 1.5 or more. In some embodiments, e.g. as shown, a pocket 10 may be cut out of the substrate 20. Typically, a diameter of the pocket "Dm" may be larger than the passage diameter "Dp" and/or flap diameter "Df". In some embodiments, the first membrane layer 15a and/or second membrane layer 15b may be covered by a piezoelectric layer 40L. In other or further embodiments, also other layers may be present, e.g. a top electrode 40e1 and/or bottom electrode 40e2 as indicated in FIG. 5A.

In some embodiments (not shown), the flap forming part of the one-way valve comprises piezoelectric material. For example, the embodiment shown could be modified to apply the piezoelectric layer 40L to the second membrane layer 15b. In other or further embodiments, the one way valve (flap or otherwise) is actively controlled to open and close at particular intervals of the (periodically) vibrating membrane, e.g. opening and closing when the flexible membrane moves towards and away from the pocket, respectively. For example, piezoelectric material on the flap can be used to actuate the valve. In one embodiment, a separate electrical connection (channel) to the piezoelectric material of the flap may be provided. For example, the flap is actuated by flipping hot and ground electrode connections, controlling the poling direction (e.g. flipping it). Alternatively, or additionally the membrane can be actuated to vibrate at a first resonance frequency and the flap actuated to vibrate at a second resonance frequency. In some embodiments, both piezoelectric material layers (in the membrane and flap) can be addressed using the same channel, e.g. actuating both using a signal consisting of at least the two resonance frequencies.

For the purpose of clarity and a concise description, features are described herein as part of the same or separate embodiments, however, it will be appreciated that the scope of the invention may include embodiments having combinations of all or some of the features described. The various elements of the embodiments as discussed and shown offer certain advantages, such as achieving and maintaining temporary non-destructive physical contact over a large surface for flexible large area devices applied to a curved or flat surface, such as ultrasound medical diagnostic devices. Of course, it is to be appreciated that any one of the above embodiments or processes may be combined with one or more other embodiments or processes to provide even further improvements in finding and matching designs and advantages. It is appreciated that this disclosure offers particular advantages to controlling adhesion of devices to various surfaces, and in general can be applied for any application where adhesive contact between surfaces or devices is desired.

In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. Where one claim refers to another claim, this may indicate synergetic advantage achieved by the combination of their respective features. But the mere fact that certain measures are recited in mutually different claims does not indicate that a combination of these measures cannot also be used to advantage. The present embodiments may thus include all working combinations of the claims wherein each claim can in principle refer to any preceding claim unless clearly excluded by context.

The invention claimed is:

1. A device for adhering by suction to a target surface, the device comprising:
a substrate having a contact surface configured for contacting the device to the target surface;
a plurality of pockets distributed across the contact surface, wherein each one of the plurality of pockets is formed by a pocket surface extending to the contact surface and has an open side that, in use, faces and is closed off by the target surface, and wherein each pocket of the plurality of pockets comprises:
a flexible membrane forming at least part of the pocket surface; and
a one-way valve formed through the pocket surface, wherein the one-way valve is:
disposed between the pocket and an environment, and
configured to direct, in use, contents of the pocket via an opening in the one-way valve to the environment; and
an actuator integrated with at least one pocket of the plurality of pockets,
wherein the actuator is configured to actuate the flexible membrane of the at least one pocket, and
wherein actuating the actuator to actuate the flexible membrane of the at least one pocket causes contents of the at least one pocket to be discharged via the one-way valve of the at least one pocket, thereby providing a suction relation between the contact surface of the device and the target surface.

2. The device according to claim 1, wherein the one-way valve is formed through the flexible membrane.

3. The device according to claim 2, wherein the one-way valve comprises a flap configured to:
open a passage out of the pocket when air flows in a first direction out of the pocket as a result of the flexible membrane being actuated; and
close, the passage that is currently open, when air flows into the pocket through the one-way valve.

4. The device according to claim 3, wherein the flexible membrane and the flap forming the one-way valve are made of a same material.

5. The device according to claim 1, wherein the actuator is disposed on the flexible membrane.

6. The device according to claim 5, wherein the actuator comprises a polymer based piezoelectric layer adhered to the flexible membrane, and wherein the flexible membrane that includes the piezoelectric layer is more flexible than the substrate.

7. The device according to claim 1, wherein the actuator is configured to vibrate at a resonance frequency of the flexible membrane.

8. The device according to claim 1, wherein the substrate is formed as a flexible sheet.

9. The device according to claim 1, wherein a volume of the pocket is less than ten millimeters cubed.

10. The device according to claim 1, wherein the substrate is formed as a sheet with a matrix of more than a hundred pockets, each pocket having a volume of less than one cubic millimeter.

11. The device according to claim 1, further comprising one or more active components disposed between the pockets and configured to transmit or receive acoustical signals into the target surface for inspecting a target volume below the target surface.

12. An ultrasound device comprising:
a substrate having a contact surface configured for contacting the device to a target surface;
a plurality of pockets distributed across the contact surface, wherein each one of the plurality of pockets is formed by a pocket surface extending to the contact surface and has an open side that, in use, faces and is closed off by the target surface, and wherein each pocket of the plurality of pockets comprises:
a flexible membrane forming at least part of the pocket surface; and
a one-way valve formed through the pocket surface, wherein the one-way valve is:
disposed between the pocket and an environment, and
configured to direct, in use, contents of the pocket via an opening in the one-way valve to the environment; and
an actuator integrated with at least one pocket of the plurality of pockets,
wherein the actuator is configured to actuate the flexible membrane of the at least one pocket,
wherein actuating the actuator to actuate the flexible membrane of the at least one pocket causes contents of the at least one pocket to be discharged via the one-way valve of the at least one pocket, thereby providing a suction relation between the contact surface of the device and the target surface,
wherein the ultrasound device comprises one or more active components disposed between pockets of the plurality of pockets, and
wherein the one or more active components are configured to transmit or receive acoustical signals into the target surface for inspecting a target volume below the target surface.

13. A method for adhering a device to a target surface, wherein the device comprises:
a substrate having a contact surface;
a plurality of pockets distributed across the contact surface, wherein each one of the plurality of pockets is formed by a pocket surface extending to the contact surface and has an open side, that, in use, faces and is closed off by the target surface, and wherein each pocket of the plurality of pockets comprises:
a flexible membrane forming at least part of the pocket surface; and
a one-way valve formed through the pocket surface, wherein the one-way valve is:
disposed between the pocket and an environment, and
configured to direct, in use, contents of the pocket via an opening in the one-way valve to the environment; and
an actuator integrated with at least one pocket of the plurality of pockets,
wherein the actuator is configured to actuate the flexible membrane of the at least one pocket,
wherein actuating the actuator to actuate the flexible membrane of the at least one pocket causes contents of the at least one pocket to be discharged via the one-way valve of the at least one pocket, thereby providing a suction relation between the contact surface of the device and the target surface; and
wherein the method comprises:
contacting the contact surface of the substrate with the target surface, wherein the target surface closes the open sides of the pockets; and
actuating, by the actuator, the flexible membrane of the at least one pocket to cause contents of the at least one pocket to be discharged via the one-way valve of the at least one pocket to the environment through the pocket surface of the at least one pocket, thereby providing a suction relation between the contact surface of the device and the target surface.

14. The method according to claim 13, wherein the device is detached after adhering by deactivating the actuator and allowing air to leak back into the plurality of pockets from the environment.

15. The method according to claim 13, wherein the one-way valves are formed through the respective flexible membrane.

16. The method according to claim 13, wherein the one-way valves each comprises a respective flap configured to:
open a respective passage out of a respective pocket of the pockets when air flows in a first direction out of the respective pocket as a result of the respective flexible membrane being actuated; and
close, the passage that is currently open, when air flows into the respective pocket through the respective one-way valve in an opposite direction.

17. The method according to claim 16, wherein the flexible membranes and the flaps forming the one-way valves are made of a same material.

18. The method according to claim 15, wherein the actuator is disposed on the flexible membrane of the at least one pocket.

19. The method according to claim 18, wherein the actuator comprises a polymer based piezoelectric layer adhered to the flexible membrane of the at least one pocket, and wherein the flexible membrane that includes the piezoelectric layer is more flexible than the substrate.

* * * * *